United States Patent [19]
Rostek, Jr. et al.

[11] Patent Number: 5,374,689
[45] Date of Patent: Dec. 20, 1994

[54] RUBBER COMPOSITIONS CONTAINING 2-PYRAZINE SULFENAMIDES

[75] Inventors: Charles J. Rostek, Jr., Bentleyville; Horng-Jau Lin, Wadsworth; David J. Sikora, Hudson, all of Ohio

[73] Assignee: Monsanto Company, St. Louis, Mo.

[21] Appl. No.: 53,970

[22] Filed: May 4, 1993

Related U.S. Application Data

[63] Continuation-in-part of Ser. No. 894,677, Jun. 5, 1992, abandoned.

[51] Int. Cl.$^5$ ............................................. C08C 19/20
[52] U.S. Cl. .................. 525/332.7; 525/329.3; 525/331.8; 525/348
[58] Field of Search ............. 525/329.3, 331.8, 332.7

[56] References Cited

U.S. PATENT DOCUMENTS 2,382,769 8/1945 Armstrong.

FOREIGN PATENT DOCUMENTS 795174 5/1958 United Kingdom.
1342046 12/1973 United Kingdom.

Primary Examiner—Christopher Henderson
Attorney, Agent, or Firm—W. W. Brooks; G. B. Seward

[57] ABSTRACT

Thiols, or thiolate salts, disulfides and sulfenamides of certain pyrazines are effective accelerators in the sulfur vulcanization of rubber. These compounds, based on 2-pyrazine, show improved rates of vulcanization compared with known sulfenamide accelerators.

4 Claims, 1 Drawing Sheet

VULCANIZATION PARAMETERS

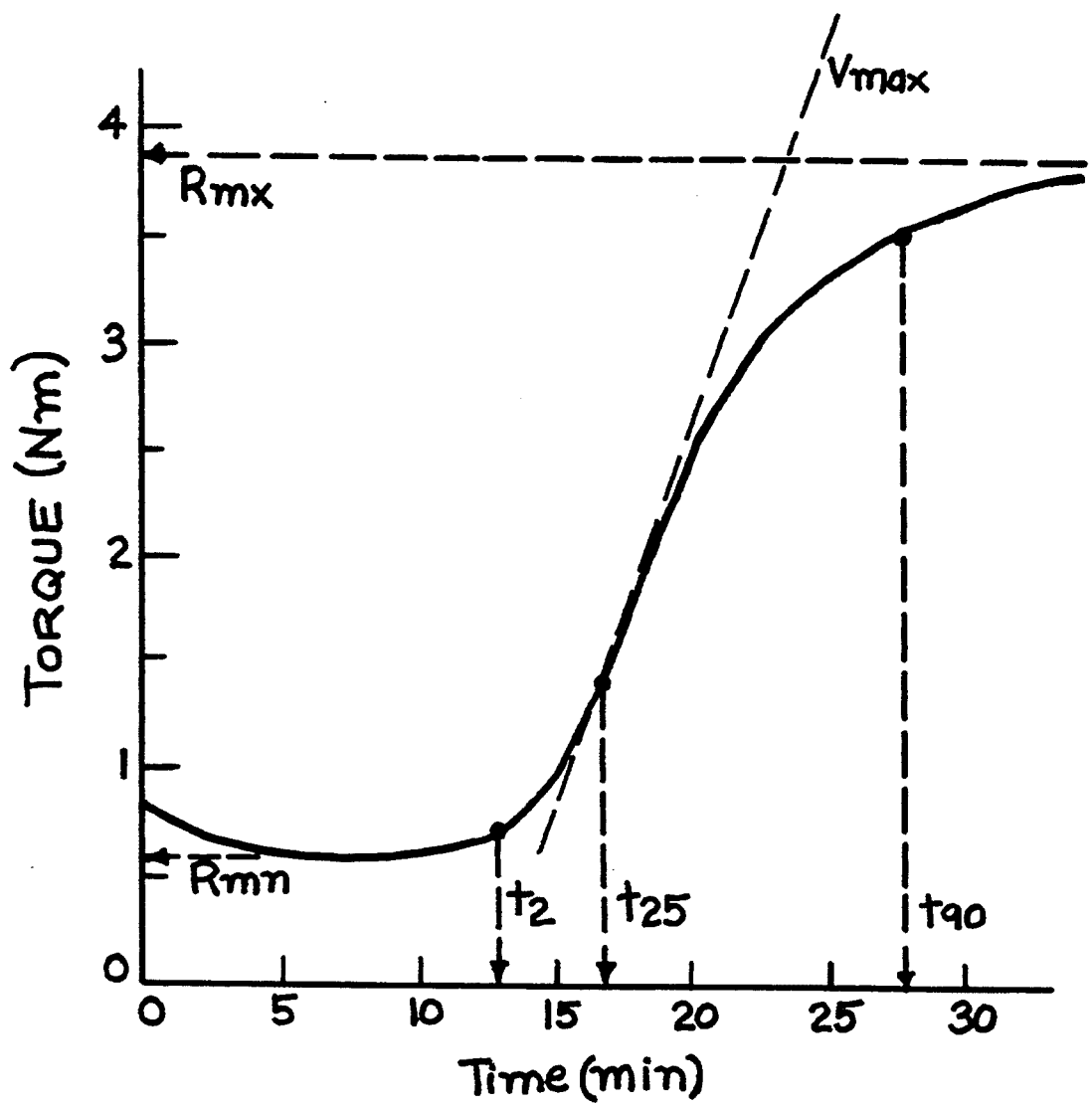
VULCANIZATION PARAMETERS

5,374,689

RUBBER COMPOSITIONS CONTAINING 2-PYRAZINE SULFENAMIDES

This application is a continuation-in-part of application Ser. No. 07/894,677, filed Jun. 5, 1992, now abandoned.

FIELD OF THE INVENTION

This invention relates to certain pyrazine thiols, disulfides and sulfenamides and to their use in rubber.

BACKGROUND

A number of heterocyclic sulfenamides, thiols and disulfides have been well known, as has been their use in the vulcanization of rubber. The best known and most widely used are based on benzothiazole. Thus, the benzothiazole sullenamides, such as N-t-butyl-2-benzothiazole sulfenamide (TBBS) and N-cyclohexyl-2-benzothiazole sulfenamide (CBS) have become standard accelerators of vulcanization. Similarly, the thiol derivative, 2-mercaptobenzothiazole (MBT) and the disulfide derivative, 2,2'-benzothiazole disulfide (MBTS), are standards of the industry.

To a lesser degree, other N-heterocycles have been suggested as the basis for sulfenamides. For example, British Patent 795,174 describes a process for making a large variety of sulfonamide compounds for use as diuretics and antibacterial agents in which the sulfenamide equivalent is first made as an intermediate. Twenty-six different basic heterocycles are suggested, and a wide variety of substituents and fused ring variations are included, as well.

Similarly, British Patent 1,342,046 discloses a process for making heterocyclic sulfenamides, based on diazine, triazine and pyridine thiols, encompassing an unlimited number of possible compounds, suggested to be effective vulcanization accelerators for rubber.

SUMMARY OF THE INVENTION

It has now been found that thiols, disulfides and sulfenamides based on certain pyrazyl moieties are particularly effective accelerators for the vulcanization of natural and synthetic rubber. More particularly, 2-pyrazine thiols, disulfides and sulfenamides have been found to have superior accelerating effect on the vulcanization of natural and synthetic rubber, compared with similar compounds based on other heterocycles.

The compounds of the present invention when utilized as accelerators for curing natural rubber, synthetic rubbers such as polybutadiene, EPDM or styrene-butadiene rubber, blends of rubbers such as natural rubber and polybutadiene, styrene-butadiene rubber and polybutadiene, or combinations thereof, result in improved cure rates as indicated by t90-t2 values, t25-t2 values and maximum rate of vulcanization (Vmax), better scorch delay, higher extent of cure (cure efficiency), and reduced reversion in comparison with traditional or conventional sulfenamide accelerators. Increased cure rates are very desirable since faster rates of production of rubber articles can be obtained. Molded rubber articles, such as tires, can thus be removed from the mold at earlier times without the danger of undercure. While it is generally possible to increase the cure rate of a rubber compound (up to a point) by using combinations of accelerators and/or higher levels of accelerators, these changes are often accompanied by unacceptable losses of scorch delay. Longer scorch delay is desirable to provide a longer time for the rubber article to be shaped and molded at processing temperatures before the onset of vulcanization. Reduced reversion is desirable because it results in a more stable network which imparts more favorable physical properties, especially to natural rubber vulcanizates. Higher extents of cure may negate the use of sulfur donors.

BRIEF DESCRIPTION OF THE DRAWING

The drawing is a typical rheograph showing the parameters of the vulcanization reaction.

DETAILED DESCRIPTION OF THE INVENTION

The compounds of the invention, which are used in rubber compositions to produce improved vulcanization behavior and/or improved vulcanizate properties, are based on 2-pyrazine (2-(1,4-diazine)).

A general formula for the compounds of the invention is

$$(PzS)_x(NRR')_yR''_z$$

wherein Pz is 2-pyrazyl, optionally substituted on the nucleus by one or more halogen atoms, or lower alkoxy or hydroxyl groups; R is H or $C_{1-8}$ alkyl, $C_{3-8}$ cycloalkyl, phenyl, $C_{7-12}$ aralkyl or $C_{7-12}$ alkaryl; R' is H or R, or R and R' together with N form a heterocyclic ring; x can be 1 or 2, y can be 0 or 1 and z can be 0 or 1; provided that when x is 2, both y and z are 0, when x is 1 and y is 1, z is 0; and when x is 1 and y is 0, z is 1 and R" is H or a cation. This general formula encompasses the thiols and disulfides as well as the sulfenamides of the invention.

The thiol versions of these compounds have an —SH group attached at the indicated position, and include 2-pyrazine thiol and its nucleus-substituted analogues. It is understood that the incorporation into the compositions of the invention of these thiols can include their use in salt form; that is, as metal salts of these thiols (e.g., zinc thiolate salts) or quaternary ammonium salts of these thiols.

Similarly, the disulfides of the invention include 2,2'-dipyrazine disulfide and nucleus-substituted analogues thereof.

The sulfenamide compounds of the invention all have a sulfenamide group attached at the 2 position, such that this sulfenamide group is based on a primary or secondary amine. The primary amines which can be used include $C_{1-8}$ alkyl amines such as methylamine, ethylamine, n-propylamine, isopropylamine, n-butylamine, sec-butylamine, isobutylamine, t-butylamine, n-amylamine, t-octylamine and the like; $C_{3-8}$ cycloalkylamines such as cyclopropylamine, cyclohexylamine, cyclooctylamine and the like; phenylamine (aniline); $C_{7-12}$ aralkylamines such as benzylamine and the like; and $C_{7-12}$ alkarylamines such as p-t-butylaniline and the like. Secondary amines include diisopropylamine, dicyclohexylamine and the like.

As indicated, one or more non-reactive substituents can be present at the open positions on the pyrazine ring, such as halogen, lower alkoxy or hydroxyl groups.

Preferred sulfenamides of the invention are those made from isopropylamine, t-butylamine or cyclohexylamine; and thus include N-isopropyl-2-pyrazine sulfenamide, N-t-butyl-2-pyrazine sulfenamide, N-cyclohexyl-2-pyrazine sulfenamide and the like.

The sulfenamides of the invention can be prepared from the respective thiol or disulfide by treatment with amine in the presence of silver nitrate or an oxidizing agent such as sodium hypochlorite or oxygen.

The 2-pyrazine compounds of the present invention can be used as primary or auxiliary accelerators in the vulcanization of rubber. Generally any type of sulfur vulcanizable rubber can be utilized such as natural rubber, synthetic rubber, various blends of synthetic rubber and combinations thereof. Natural rubber is usually obtained from *Hevea brasiliensis* trees, and generally grown in the tropics. Synthetic rubbers include those made from various dienes such as those having from 4 to 12 carbon atoms and preferably from 4 to 8 carbon atoms including 1,3-butadiene, isoprene, 2,3-dimethyl-1,3-butadiene, 2-methyl-1,3-pentadiene, 3,4-dimethyl-1,3-hexadiene, 4,5-diethyl-1,3-octadiene, phenyl-1,3-butadiene, pentadiene, hexadiene, octadiene, and the like. Synthetic rubbers also include copolymers made from the immediately above-noted dienes having from 4 to 12 carbon atoms with a vinyl substituted aromatic compound having from 8 to 20 carbon atoms such as styrene, alpha-methylstyrene, 4-n-propylstyrene, 4-t-butylstyrene, and the like, as well as copolymers made from the above dienes and acrylonitrile.

Another class of synthetic rubbers which can be utilized in the present invention are EPDM rubbers. These are polymers made from ethylene, propylene, and a minor proportion of a non-conjugated diene monomer such as ethylidenenorbornene, dicyclopentadiene, 1,4-hexadiene and the like. Butyl rubbers, which are copolymers from isobutylene and a minor proportion of isoprene, can be used, as well as their halogenated derivatives, such as chlorobutyl or bromobutyl rubber. Other sulfur vulcanizable rubbers known to the art and to the literature can also be utilized.

The rubber polymers made from conjugated dienes or copolymers of a conjugated diene or the vinyl substituted aromatic are preferably "elastomeric" materials, that is they conform, when vulcanized, to the definition of an elastomeric or rubber material found in ASTM D 1566.

As noted above, either natural rubber, one or more synthetic rubbers, that is either a single type of synthetic rubber or blends of two or more synthetic rubbers, as well as a blend of natural rubber and one or more synthetic rubbers can be cured utilizing one of the diazine compounds of the present invention as a primary accelerator. When utilized as a primary accelerator, the amount thereof is generally from about 0.1 to about 10 parts and preferably from about 0.2 to about 2.0 parts by weight per 100 parts by weight (phr) of the rubber polymer or blend. When the 2-pyrazine compounds of the invention are utilized as accelerators for curing rubber compounds, the natural or synthetic rubber compositions of the present invention generally contain other conventional compounding ingredients in conventional amounts, both of which are well known to the art and to the literature. Sulfur, in amounts of from 0.5 to 5 phr, is usually employed. Also, various fillers and reinforcing agents, such as clay, silica, and carbon black, can be utilized in amounts from 5 up to about 200 phr. Various oils, for example aromatic, naphthenic, or paraffinic, can be utilized to plasticize the rubber in amounts from 5 up to about 200 phr. Various activators such as zinc oxide, stearic acid, and the like, can also be used in amounts up to about 15 or more phr. Various antidegradants, and the like, well known in the art, can also be utilized. Such materials are generally mixed into the rubber by utilizing a mill, a Banbury mixer, or the like.

The rubber compositions can be used in a large number of applications, including finished articles such as tires.

The 2-pyrazine compounds of the present invention when utilized as primary accelerators with rubber have been found to yield very much improved cure rates and cure states, i.e., lower t25-t2 or t90-t2 values and higher Vmax values and higher Rmax values. The improved cure rate values were generally superior to the values obtained utilizing conventional thiazole sulfenamide primary accelerators such as N-cyclohexyl-2-benzothiazole sulfenamide, N-t-butyl-2-benzothiazole sulfenamide, N-t-butyl-2-benzothiazole sulfenimide and the like. Another unexpected result was that improved scorch delay was obtained for the 2-pyrazine sulfenamides. Yet another unexpected result was reduced reversion values as set forth in the following data. However, it is also found to be advantageous to use the accelerators of the invention as auxiliary accelerators, in combination with other well-known conventional accelerators, which include the guanidines, such as diphenylguanidine (DPG) or di-ortho-tolylguanidine (DOTG), the various thiazoles, such as 2-mercaptobenzothiazole and 2,2'-benzothiazole disulfide; benzothiazole sulfenamides, such as N-cyclohexyl-2-benzothiazole sulfenamide, N,N-dicyclohexyl-2-benzothiazole sulfenamide, N,N-diethyl-2-benzothiazole sulfenamide. N,N-diisopropyl-2-benzothiazole sulfenamide, N-oxydiethylene-2-benzothiazole sulfenamide, N-isopropyl-2-benzothiazole sulfenamide and N-t-butyl-2-benzothiazole sulfenamide. When EPDM rubber is vulcanized, a thiazole accelerator is generally used in combination with a thiuram accelerator. Examples of conventional thiuram accelerators include N,N'-dimethyl-N,N'-diphenylthiuram disulfide, dipentamethylenethiuram hexasulfide, tetramethylthiuram monosulfide, tetraethylthiuram disulfide, tetrabutylthiuram disulfide, tetramethylthiuram disulfide, and metal salts of the corresponding dithiocarbamic acids, such as those of zinc, copper, tellurium, etc.

From 0.1 to 0.5 phr of the accelerators of the invention can be used, together with larger amounts (from 0.2 to 2.0 phr) of one or more conventional accelerators. Conversely, a small (0.1 to 0.5 phr) amount of one or more conventional accelerators can be used with a larger amount of one of the accelerators of the invention.

The invention will be better understood by reference to the following examples in which all parts are by weight and all temperatures are in degrees Celsius, unless otherwise specified.

EXAMPLES

Various 2-pyrazine thiols, disulfides and sulfenamides of the present invention were tested in accordance with appropriate ASTM procedures for rubber. Parameters which characterize vulcanization were taken from ODR (oscillating disc rheometer) cure curves ("rheographs"), which were obtained for vulcanization at 153°. As is graphically shown in the drawing, the parameters Rmin and Rmax are the minimum rheometer torque (before the onset of vulcanization) and the maximum rheometer torque (due to vulcanization), respectively. The parameter t2 is the time required for an increase (over Rmin) in rheometer torque of 2.2 dNm (2.0 in-lb); t25 is the time required for the occurrence of 25 percent of the increase in torque due to vulcanization (time at which torque equals (Rmax−Rmin)0.25+Rmin); t90 is the time required for the occurrence of 90 percent of the increase in torque due to vulcanization (time at which torque equals (Rmax−Rmin)0.9+Rmin). Vmax is the maximum slope of the vulcanization curve divided by Rmax−Rmin expressed in terms of percent per minute.

The invention will be better understood by reference to the following examples in which all parts are per 100 parts by weight of rubber (phr) and all temperatures are in degrees Celsius, unless otherwise specified.

Preparation of Rubber Masterbatches for Accelerator Evaluation

The various examples of 2-pyrazine accelerators which were prepared were tested in typical NR and SBR carbon-black reinforced compounds.

An SBR rubber masterbatch was prepared, based on SBR-1500, containing the following ingredients:

| SBR Masterbatch | Parts |
|---|---|
| SBR-1500 | 100.0 |
| Carbon Black N-330 | 50.0 |
| Circosol 4240, a Naphthenic Oil, ASTM D2226, Type 103 | 10.0 |
| Zinc Oxide | 4.0 |
| Stearic Acid | 2.0 |
| | 166.0 |

The SBR masterbatch was prepared by mixing the above-noted components in a Banbury mixer according to standard techniques. Subsequently, various accelerators, sulfur, and an antidegradant were added on a laboratory roll mill in the amounts set forth hereinbelow and blended by using standard laboratory mill mixing techniques:

| | Parts |
|---|---|
| SBR-Masterbatch | 166.0 |
| SANTOFLEX 13 | 2.0 |
| Sulfur | 2.0 |
| Accelerators | As indicated |

SBR-1500 is a cold emulsion-polymerized, non-pigmented styrene/butadiene copolymer rubber containing nominally 23.5 percent bound styrene;

SANTOFLEX ® 13 is N-(1,3-dimethylbutyl)-N'-phenyl-para-phenylenediamine, an antidegradant.

In a similar manner, a natural rubber masterbatch was made:

| Natural Rubber Masterbatch | Parts |
|---|---|
| Natural Rubber (SMR-CV) | 100.0 |
| Carbon Black N-330 | 50.0 |
| Naphthenic Oil; Circosol 4240 | 5.0 |
| Zinc Oxide | 5.0 |
| Stearic Acid | 2.0 |
| Total | 162.0 |

The natural rubber masterbatch was blended with the following compounds according to standard laboratory mill-mixing techniques:

| | Parts |
|---|---|
| Natural Rubber Masterbatch | 162.0 |
| SANTOFLEX 13 | 2.0 |
| Sulfur | 2.5 |
| Accelerators | As indicated |

The following Examples 1–3 show the preparation of 2-pyrazine compounds of the invention. Following this are Tables I–III which set forth the test data for rubber compositions of the invention (and the control compositions).

EXAMPLE 1

N-t-Butyl-2-Pyrazine Sulfenamide

Silver nitrate (3.82 g, 0.023 moles) was stirred with ethanol (200 ml) and t-butylamine (12 ml) for approximately five minutes and then 2,2'-dipyrazine disulfide (5 g, 0.023 moles) was added. An immediate turbulence resulted. The reaction mixture was allowed to stir for 47 hours at room temperature.

The precipitated solid, assumed to be the silver salt of 2-mercaptopyrazine, was collected by filtration and the organic solvent removed by distillation under reduced pressure. The resulting oil (7.2 g) froze when stored in the refrigerator. The yield of precipitated solid isolated above was 4.99 g (101.4% of theory). The oil product was brought to room temperature and stirred with anhydrous ether (200 ml) for two hours. The undissolved solid was collected by filtration and air dried. It was assumed to be t-butylammonium nitrate (2.91 g, 95% theoretical yield). Evaporation of the ether gave an oil which spontaneously crystallized to a solid (3.4 g, m.p. 44°–52° C.) after filtration and evaporation of its solution in methylene chloride. It was characterized by liquid chromatography and NMR spectroscopy: (δ, multiplicity, assignment, integration) 8.9–8.2, m, aromatic, 3 H; 3.3, s, NH, 1 H; 1.2, s, t-butyl, 9 H.

EXAMPLE 2

N-i-Propyl-2-Pyrazine Sulfenamide

The procedure of the previous example was followed using isopropylamine (9.6 ml) in place of t-butylamine and stirring the ethanolic reaction mixture for 24 hours at room temperature. The residual product after removal of the ether by distillation under reduced pressure (3.55 g, 93% of theory) remained an oil after prolonged storage in the freezer. It was pure by liquid chromatographic analysis and NMR spectroscopy: (δ, multiplicity, assignment, integration) 8.7–8.2, m, aromatic, 3 H; 3.3, m, NH and methine, 2 H; 1.1 and 1.2, d, methyl 6 H.

EXAMPLE 3

2,2'-Dipyrazine Disulfide

To a solution of sodium ethoxide, prepared from sodium (6.9 g, 0.3 g atom) and ethanol (150 ml), dimethylformamide (150 ml) was added. After removing the ethanol by distillation, the residual solution was saturated with hydrogen sulfide. The deep green solution was heated with 2-chloropyrazine (17.25 g, 0.15 mole) at 100° for 3 hours, and solvent was then removed under reduced pressure. The residue was dissolved in water, then acidified with acetic acid to give a yellow precipitate which was extracted with 2N NaOH (75 ml). After filtration, acidification of the solution gave 2-mercaptopyrazine (15 g., 88%), m.p. 209°–214° C.

A solution of iodine (2.6 g) in potassium iodide (5 g) and water (20 ml) was added dropwise to a solution of 2-mercaptopyrazine (1.1 g) in 2N NaOH (10 ml). After refrigeration, the crystalline precipitate (0.6 g) was filtered off and identified as 2,2'-dipyrazine disulfide by its proton and $^{13}C$ NMR spectra and melting point, 106°–108°.

TABLE I

COMPOUNDS OF EXAMPLES 1 AND 2 IN SBR

| | Run # | | |
|---|---|---|---|
| | 1 | 2 | 3 |
| SBR Masterbatch | 166 | 166 | 166 |
| TBBS | 1.2 | — | — |
| Compound Ex. 1 | — | 1.2 | — |
| Compound Ex. 2 | — | — | 1.2 |
| Mooney Scorch, 135°, t5, min. | 27.3 | 45.1 | 40.0 |
| ODR Data @ 153° | | | |
| Rmax, Nm | 4.32 | 5.03 | 5.10 |
| Rmin, Nm | 0.57 | 0.56 | 0.55 |
| t90, min. | 24.6 | 28.7 | 26.4 |
| t2, min. | 10.0 | 14.1 | 13.3 |
| t90–t2, min. | 14.6 | 14.6 | 13.1 |
| t25, min. | 13.8 | 18.4 | 16.2 |
| t25–t2, min. | 3.8 | 4.3 | 2.9 |
| Max. Veloc. of vulc., %/min. | 11.2 | 22.8 | 27.9 |

TABLE II

COMPOUNDS OF EXAMPLES 1 AND 2 IN NATURAL RUBBER

| | Run # | | |
|---|---|---|---|
| | 4 | 5 | 6 |
| NR Masterbatch | 162 | 162 | 162 |
| TBBS | 0.6 | — | — |
| Compound Ex. 1 | — | 0.6 | — |
| Compound Ex. 2 | — | — | 0.6 |
| Mooney Scorch, 120°, t5, min. | 31.6 | 42.7 | 37.0 |
| ODR Data @ 153° | | | |
| Rmax, Nm | 3.86 | 4.31 | 4.40 |
| Rmin, Nm | 0.39 | 0.36 | 0.37 |
| t90, min. | 10.9 | 11.0 | 10.0 |
| t2, min. | 4.2 | 4.5 | 4.3 |
| t90–t2, min. | 6.7 | 6.5 | 5.8 |
| t25, min. | 5.5 | 5.7 | 5.2 |
| t25–t2, min. | 1.3 | 1.2 | 1.0 |
| Max. veloc. of vulc, %/min. | 22.0 | 33.1 | 37.4 |
| Rever., % 30 min. | 20.2 | 16.2 | 15.3 |

The test results set forth in Tables I and II show the effectiveness of the N-alkyl-2-pyrazine sulfenamides of the invention. In all instances the compounds of the invention gave better (longer) scorch times than the control; the compounds of the invention gave better (faster) cure rates than the control, higher extents of cure than the control and better reversion resistance (NR) than the control.

To demonstrate the use of the disulfide compounds of the invention as accelerators, 2,2'-dipyrazine disulfide was compared with TBBS at equal levels. Formulations and results are set forth in Table III.

TABLE III

COMPOUND OF EXAMPLE 3 IN SBR AND NATURAL RUBBER

| | Run # | | | |
|---|---|---|---|---|
| | 7 | 8 | 9 | 10 |
| SBR Masterbatch | 166 | 166 | — | — |
| NR Masterbatch | — | — | 162 | 162 |
| TBBS | 1.2 | — | 0.6 | — |
| 2,2'-Dipyrazine Disulfide (Ex. 3) | — | 1.2 | — | 0.6 |
| Mooney Scorch, 135° C., t5, min. | 24.0 | 17.5 | 12.3 | 7.8 |
| ODR Data at 153° C. | | | | |
| Rmax, Nm | 3.97 | 4.96 | 3.80 | 3.77 |
| Rmin, Nm | 0.57 | 0.58 | 0.64 | 0.62 |
| t90, min. | 24.17 | 24.84 | 12.84 | 10.00 |
| t2, min. | 11.17 | 7.50 | 5.50 | 3.83 |
| t90–t2, min. | 13.00 | 17.34 | 7.34 | 6.17 |
| t25, min. | 14.17 | 9.00 | 6.83 | 4.50 |
| t25–t2, min. | 3.00 | 1.50 | 1.33 | 0.67 |
| Max. veloc of Vulc., %/min. | 12.17 | 20.31 | 21.7 | 34.4 |

The test results set forth in Table III show the effectiveness of 2,2'-dipyrazine disulfide of the invention. Relative to the control, TBBS, this disulfide exhibits faster cure rates with equal or higher extents of cure.

It is claimed:

1. A composition containing sulfur-vulcanizable rubber and from 0.1 to 10 parts by weight per 100 parts by weight of rubber of a compound of the formula (PzS) (NRR')

wherein Pz is 2-pyrazyl; R is isopropyl, t-butyl or cyclohexyl and R' is H.

2. The composition of claim 1 wherein R is t-butyl.
3. The composition of claim 1 wherein R is isopropyl.
4. The composition of claim 1 wherein R is cyclohexyl.

* * * * *